(12) United States Patent
Glukhovsky

(10) Patent No.: US 7,877,134 B2
(45) Date of Patent: Jan. 25, 2011

(54) APPARATUS AND METHODS FOR IN VIVO IMAGING

(75) Inventor: Arkady Glukhovsky, Santa Clarita, CA (US)

(73) Assignee: Given Imaging Ltd., Yoqneam Ilite (IL)

( * ) Notice: Subject to any disclaimer, the term of this patent is extended or adjusted under 35 U.S.C. 154(b) by 629 days.

(21) Appl. No.: 10/485,620

(22) PCT Filed: Aug. 1, 2002

(86) PCT No.: PCT/IL02/00634

§ 371 (c)(1),
(2), (4) Date: Feb. 2, 2004

(87) PCT Pub. No.: WO03/011103

PCT Pub. Date: Feb. 13, 2003

(65) Prior Publication Data

US 2004/0199061 A1    Oct. 7, 2004

Related U.S. Application Data

(60) Provisional application No. 60/309,169, filed on Aug. 2, 2001.

(51) Int. Cl.
*A61B 6/00* (2006.01)
(52) U.S. Cl. .................. 600/476; 600/109; 600/160
(58) Field of Classification Search ............ 600/407, 600/476, 160, 109
See application file for complete search history.

(56) References Cited

U.S. PATENT DOCUMENTS

| | | | |
|---|---|---|---|
| 3,683,389 A | 8/1972 | Hollis | |
| 3,971,362 A | 7/1976 | Pope et al. | |
| 4,278,077 A * | 7/1981 | Mizumoto | 600/109 |
| 4,689,621 A | 8/1987 | Kleinberg | |
| 4,741,327 A | 5/1988 | Yabe | |
| 4,844,076 A | 7/1989 | Lesho et al. | |
| 5,279,607 A | 1/1994 | Schentag et al. | |
| 5,604,531 A | 2/1997 | Iddan et al. | |
| 5,819,736 A | 10/1998 | Avny et al. | |
| 5,940,126 A | 8/1999 | Kimura | |
| 6,240,312 B1 | 5/2001 | Alfano et al. | |
| 6,855,111 B2 * | 2/2005 | Yokoi et al. | 600/179 |

(Continued)

FOREIGN PATENT DOCUMENTS

DE    34 40 177    5/1986

(Continued)

OTHER PUBLICATIONS

The Radio Pill, Rowlands, et al., British Communications and Electronics, Aug. 1960, pp. 598-601.

(Continued)

*Primary Examiner*—Brian Casler
*Assistant Examiner*—Amanda Lauritzen
(74) *Attorney, Agent, or Firm*—Pearl Cohen Zedek Latzer, LLP

(57) ABSTRACT

An in vivo imaging device and method, the device including at least one illumination source; at least one image sensor; and at least two optical systems. The optical systems have different depths of focus. A first and second image are focused onto the image sensor.

15 Claims, 4 Drawing Sheets

U.S. PATENT DOCUMENTS

| | | | |
|---|---|---|---|
| 6,984,205 B2 * | 1/2006 | Gazdzinski | 600/160 |
| 7,001,329 B2 * | 2/2006 | Kobayashi et al. | 600/114 |
| 7,009,634 B2 | 3/2006 | Iddan et al. | |
| 7,116,352 B2 * | 10/2006 | Yaron | 348/45 |
| 7,118,529 B2 * | 10/2006 | Glukhovsky et al. | 600/160 |
| 2001/0035902 A1 * | 11/2001 | Iddan et al. | 348/76 |
| 2001/0051766 A1 | 12/2001 | Gazdzinski | |
| 2002/0103417 A1 * | 8/2002 | Gazdzinski | 600/109 |
| 2002/0198439 A1 * | 12/2002 | Mizuno | 600/109 |
| 2003/0025821 A1 * | 2/2003 | Bean et al. | 348/345 |
| 2003/0028078 A1 * | 2/2003 | Glukhovsky | 600/109 |
| 2003/0072011 A1 * | 4/2003 | Shirley | 356/601 |
| 2003/0114742 A1 | 6/2003 | Lewkowicz et al. | |
| 2003/0117491 A1 | 6/2003 | Avni et al. | |
| 2003/0167000 A1 * | 9/2003 | Mullick et al. | 600/424 |
| 2003/0171653 A1 * | 9/2003 | Yokoi et al. | 600/160 |
| 2003/0227547 A1 | 12/2003 | Iddan | |
| 2006/0036131 A1 * | 2/2006 | Glukhovsky et al. | 600/160 |
| 2006/0209185 A1 * | 9/2006 | Yokoi | 348/65 |
| 2007/0142710 A1 * | 6/2007 | Yokoi et al. | 600/173 |
| 2007/0255099 A1 * | 11/2007 | Yokoi et al. | 600/109 |
| 2009/0052059 A1 * | 2/2009 | Lin | 359/755 |
| 2009/0240108 A1 * | 9/2009 | Shimizu et al. | 600/109 |
| 2009/0306474 A1 * | 12/2009 | Wilson | 600/109 |

FOREIGN PATENT DOCUMENTS

| | | |
|---|---|---|
| GB | 2 291 980 | 2/1996 |
| JP | 57-45833 | 3/1982 |
| JP | HEI 3-289779 | 12/1991 |
| JP | 4109927 | 4/1992 |
| JP | HEI 4-109927 | 4/1992 |
| JP | HEI 4-180736 | 6/1992 |
| JP | 5015515 | 1/1993 |
| JP | 9-21961 | 1/1997 |
| JP | 9-122068 | 5/1997 |
| JP | 10-179516 | 7/1998 |
| JP | 2001224553 | 8/2001 |
| WO | WO 92/21307 | 12/1992 |
| WO | WO 98/11816 | 3/1998 |
| WO | WO 00/76391 | 12/2000 |
| WO | WO 01/08548 | 2/2001 |
| WO | WO 01/35813 | 5/2001 |
| WO | WO 01/50941 | 7/2001 |
| WO | WO 01/65995 | 9/2001 |
| WO | WO 01/87377 | 11/2001 |
| WO | WO 03/010967 | 2/2003 |

OTHER PUBLICATIONS

Wellesley company sends body montiors into space—Crum, Apr. 1998.

Wireless transmission of a color television moving image from the stomach using a miniature CCD camera, light source and microwave transmitter Swain CP, Gong F, Mills TN. Gastrointest Endosc 1997;45:AB40.

BBC News Online—Pill camera to 'broadcast from the gut', Feb. 21, 2000, www.news.bbc.co.uk.

Office Action from Japanse Application No. JP 2003/516344 mailed on Apr. 15, 2008.

Search Report from International Application No. PCT/IL02/00634 issued on Jul. 2, 2003.

* cited by examiner

US 7,877,134 B2

APPARATUS AND METHODS FOR IN VIVO IMAGING

CROSS-REFERENCE TO RELATED APPLICATIONS

This application is a National Phase Application of PCT International Application No. PCT/IL02/00634, International Filing Date Aug. 1, 2002, published as WO 03/011103 on Feb. 13, 2003 entitled "APPARATUS AND METHODS FOR IN VIVO IMAGING", incorporated by reference herein which in turn claims priority of US Provisional Patent Application, 60/309,169, filed Aug. 2, 2001, incorporated by reference herein.

FIELD OF THE INVENTION

The present invention relates generally to in vivo imaging devices, and more specifically to in vivo imaging devices having extended depth of field or variable depth of field.

BACKGROUND OF THE INVENTION

Devices and methods for performing in-vivo imaging of passages or cavities within a body are known in the art. Such devices may include, inter alia, various endoscopic imaging systems and devices for performing imaging in various internal body cavities.

Reference is now made to FIG. 1 which is a schematic diagram illustrating an embodiment of an autonomous in-vivo imaging device. The device 10A typically includes an optical window 21 and an imaging system for obtaining images from inside a body cavity or lumen, such as the GI tract. The imaging system includes an illumination unit 23. The illumination unit 23 may include one or more light sources 23A. The one or more light sources 23A may include a white light emitting diode (LED), or any other suitable light source, known in the art. The device 10A includes a CMOS imaging sensor 24, which acquires the images and an optical system 22 which focuses the images onto the CMOS imaging sensor 24.

The optical system 22 may include one or more optical elements (not shown), such as one or more lenses (not shown), one or more composite lens assemblies (not shown), one or more suitable optical filters (not shown), or any other suitable optical elements (not shown) adapted far focusing an image of the GI tract on the imaging sensor as is known in the art and disclosed hereinabove with respect to the optical unit 22 of FIG. 1. The optical system 22 may be attached to, or mounted on, or fabricated on or disposed adjacent to the imager light sensitive pixels (not shown) as is known in the art.

The illumination unit 23 illuminates the inner portions of the body lumen or body cavity (such as, for example the gastrointestinal cavity) through an optical Window 21. Device 10A further includes a transmitter 26 and an antenna 27 for transmitting image signals from the CMOS imaging sensor 24, and one or more power sources 25. The power source(s) 25 may be any suitable power sources such as but not limited to silver oxide batteries, lithium batteries, or other electrochemical cells having a high energy density, or the like. The power source(s) 25 may provide power to the electrical elements of the device 10A.

Typically, in the gastrointestinal application, as the device 10A is transported through the gastrointestinal (GI) tract, the imager, such as but not limited to the multi-pixel CMOS sensor 24 of the device 10A acquires images (frames) which are processed and transmitted to an external receiver/recorder (not shown) worn by the patient for recording and storage. The recorded data may then be downloaded from the receiver/recorder to a computer or workstation (not shown) for display and analysis. During the movement of the device 10A through the GI tract, the imager may acquire frames at a fixed or at a variable frame acquisition rate. For example, the imager (such as, but not limited to the CMOS sensor 24 of FIG. 1) may acquire images at a fixed rate of two frames per second (2 Hz). Other different frame rates may also be used, depending, inter alia, on the type and characteristics of the specific imager or camera or sensor array implementation that is used, and on the available transmission bandwidth of the transmitter 26. The downloaded images may be displayed by the workstation by replaying them at a desired frame rate. This way, the expert or physician examining the data is provided with a movie-like video playback, which may enable the physician to review the passage of the device through the GI tract.

Typically, the device 10A or a similar autonomous in vivo imaging device is propelled through the GI tract by the natural action of peristalsis. When the device 10A or a similar autonomous in vivo imaging device is used for imaging, some of the acquired images may be out of focus. Additionally in some of the acquired images, a part or parts of the acquired image may be out of focus because of a possibly limited depth of field obtainable by the optical system 22. For example, if the optical system 22 includes a lens (not shown in detail) having a limited depth of field, and the imaged object (such as, for example, the wall of the GI tract) or a portion thereof was not disposed at a distance which is Within the depth of field range of the lens, the acquired image or parts thereof may be blurred or not depicted sharply.

It may therefore be desirable to decrease the number or the percentage of acquired images which are not acceptably focused or which have a reduced sharpness or detail due to out of focused imaging.

SUMMARY

Embodiments of the present invention provide an in vivo imaging device and method. In one embodiment, a device includes an illumination source; an image sensor; and at least two optical systems. The optical systems have different depths of focus. A first and second image are focused onto the image sensor.

BRIEF DESCRIPTION OF THE DRAWINGS

The invention is herein described, by way of example only, with reference to the accompanying drawings in which like components are designated by like reference numerals, wherein.

DETAILED DESCRIPTION OF THE INVENTION

One approach which may be used to solve the image sharpness problem of in vivo imaging devices is to use an optical system such as, but not limited to, a lens or a lens assembly having a wide depth of field range. Typically, wide angle lenses may be used. Such lenses may be compound multi-element lenses or other lens types.

Another approach may be to use a plurality of lenses within the same imaging device.

Figure 2:
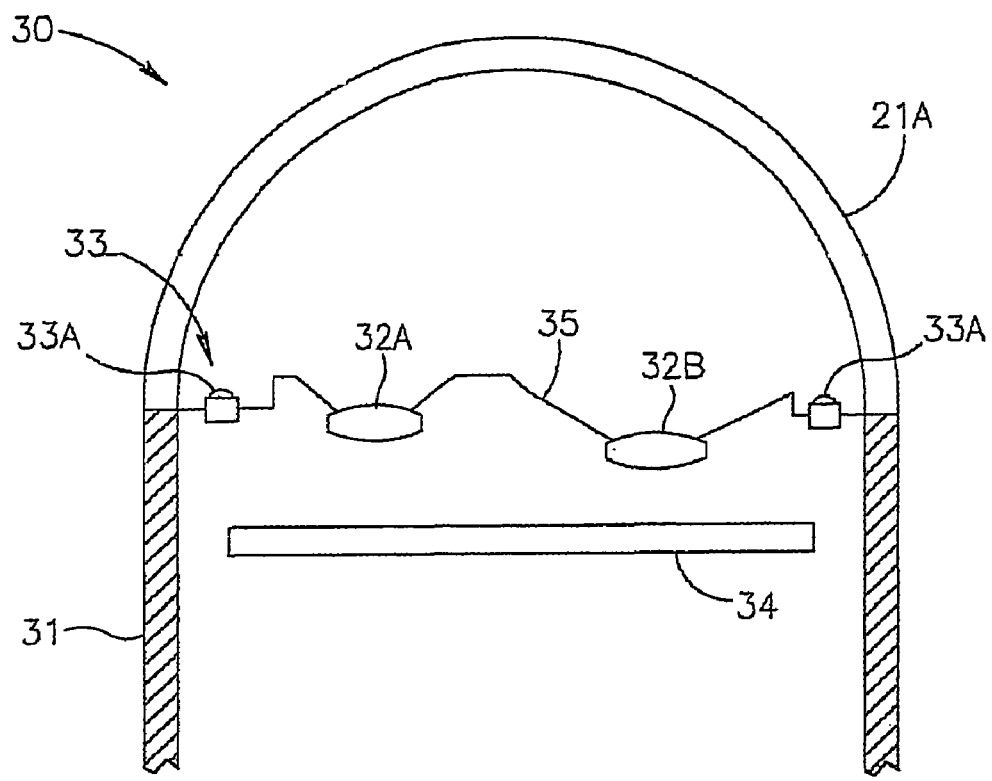
FIG. 2 is a schematic cross-sectional view of part of an in-vivo imaging device having two optical systems and a single imager, in accordance with an embodiment of the present invention.

Reference is now made to FIG. 2 which is a schematic cross-sectional view of part of an in-vivo imaging device having two Optical systems and a single imager, in accordance with an embodiment of the present invention.

The in vivo imaging device 30 (only part of which is illustrated in FIG. 2) includes an imaging sensor 34. The imaging sensor 34 may be a CMOS pixel array sensor similar to the CMOS imaging sensor 24 of FIG. 1, or may be any other type of suitable imaging sensor known in the art; for example, a CCD may be used.

The device 30 includes a housing 31 and an optical window 21A attached to the housing 31. If the device 30 is implemented as a swallowable capsule, the housing 31 may be, for example, a capsule-like housing, as disclosed in detail in U.S. Pat. No. 5,604,531 to Iddan et al., and/or WO 01/65995 to Glukhovsky et al. The system and method of the present invention may be used with other swallowable devices. If the device 30 is implemented as, for example, an endoscope-like device or a catheter-like device, the housing 31 may be an extended elongated flexible device (the extended device is not shown in its entirety for the sake of clarity of illustration). Such devices may be shaped as, for example, elongated flexible devices for insertion into a body cavity or body lumen of a human patient or an animal.

The optical window 21A may be a transparent optical dome as disclosed in WO 00/76391 to Glukhovsky et al. but may be any type of suitable optical window.

The device 30 may include an illumination unit 33 which may include one or more light sources 33A. The light sources 33A may be "white" LED sources as disclosed in WO 01/65995 to Glukhovsky et al. but may also be any other light sources suitable for providing illumination for in vivo imaging, such as but not limited to the light sources disclosed in U.S. Pat. No. 5,604,531 to Iddan et al. The device 30 may include two optical systems 32A and 32B. The optical systems 32A and 32B may be attached to or mounted in a baffle 35, or otherwise suitably attached to the housing 31 of the device 30 or to any other suitable structure included in the device 30 (such as for example, the imaging sensor 34). The baffle 35 may be shaped to prevent light emitted from the light sources 33A from directly reaching the optical systems 32A and 32B, while allowing light reflected from the imaged object, such as but not limited to, the intestinal wall (not shown) to reach the optical systems 32A and 32B. The device 30 may be of other configurations and include other combinations of components. For example, the baffle 35 need not be used.

The imaging sensor 34 may be disposed adjacent to the optical systems 3A and 32B, or may be also attached thereto.

The optical systems 32A and 32B may be typically single lenses, composite (multi-element) lenses, or any suitable combination of optical elements which are suitable for forming images of the imaged object, (such as but not limited to, the intestinal wall) and projecting the images onto the surface of the imaging sensor 34.

The depth of field range of the optical system 32A is different than the depth of field range of the optical system 32B. For example, the focal length of the optical system 32A may be longer than the focal length of the optical system 32B. Each of the optical systems 32A and 32B projects an image on the surface of the imaging sensor 34. According to one embodiment, the images projected by the optical systems 32A and 32B do not overlap.

Thus, after the pixels of the imaging sensor 34 are scanned (read out) and the data is transmitted to an outside receiver/recorder as disclosed hereinabove, the resulting image may have two typically non-overlapping parts. One image part corresponds to the image projected on the imaging sensor by the optical system 32A, and the other image part corresponds to the image projected on the imaging sensor by the optical system 32B.

Because of the different focal length of the two different optical systems 32A and 32B, even if one image part is not properly focused the other image part may be in focus due to the larger depth of field range of the optical system having the shorter focal length. Thus, the chance of obtaining at least one acceptably focused image is increased relative to the chance in a similar in vivo imaging device which includes only a single optical system 32A (for example, having a larger focal length and a narrower depth of focus) of which may include a plurality of optical systems.

Figure 2A:
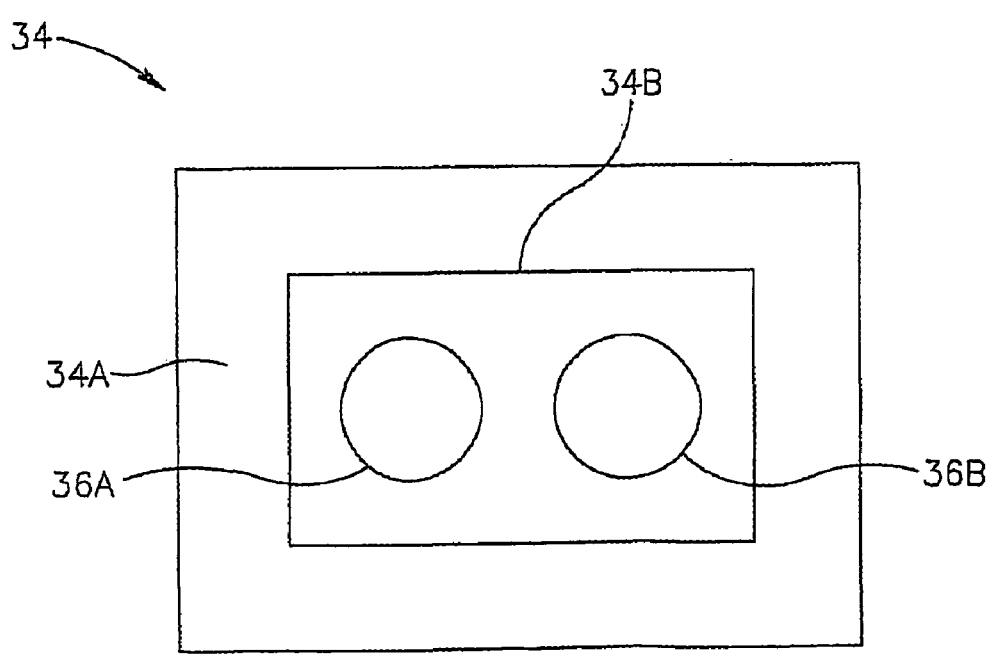
FIG. 2A is a schematic front view of the surface of the imaging sensor of the device illustrated in FIG. 2, schematically illustrating non-overlapping images projected on the surface of the imaging sensor.

Reference is now made to FIG. 2A which is a schematic front view of the surface of the imaging sensor of the device illustrated in FIG. 2, schematically illustrating non-overlapping images projected on the surface of the imaging sensor.

In FIG. 2A, the surface 34A represents a top view of the surface of the entire imaging sensor 34. The surface 34B schematically represents the imager area part comprising the light sensitive pixels (the pixels are not shown in detail). The part of the imager surface surrounding the area 34B may include the support circuitry for performing readout of the pixels and other electronic support circuitry such as clocking circuitry and the like, as is known in the art.

The circular areas 36A and 36B schematically represent the area of the images projected on the surface 34B by the optical systems 32A and 32B, respectively. The areas 36A and 36B do not overlap.

It will be appreciated by those skilled in the art that while the device 30 of FIG. 2 may provide a solution to the depth of focus problem, it may not make the best use of the light sensitive pixel areas 34B available in the imaging sensor 34. This may be due to the requirement for non-overlapping of the projected a image areas 36A and 36B.

Figure 3:
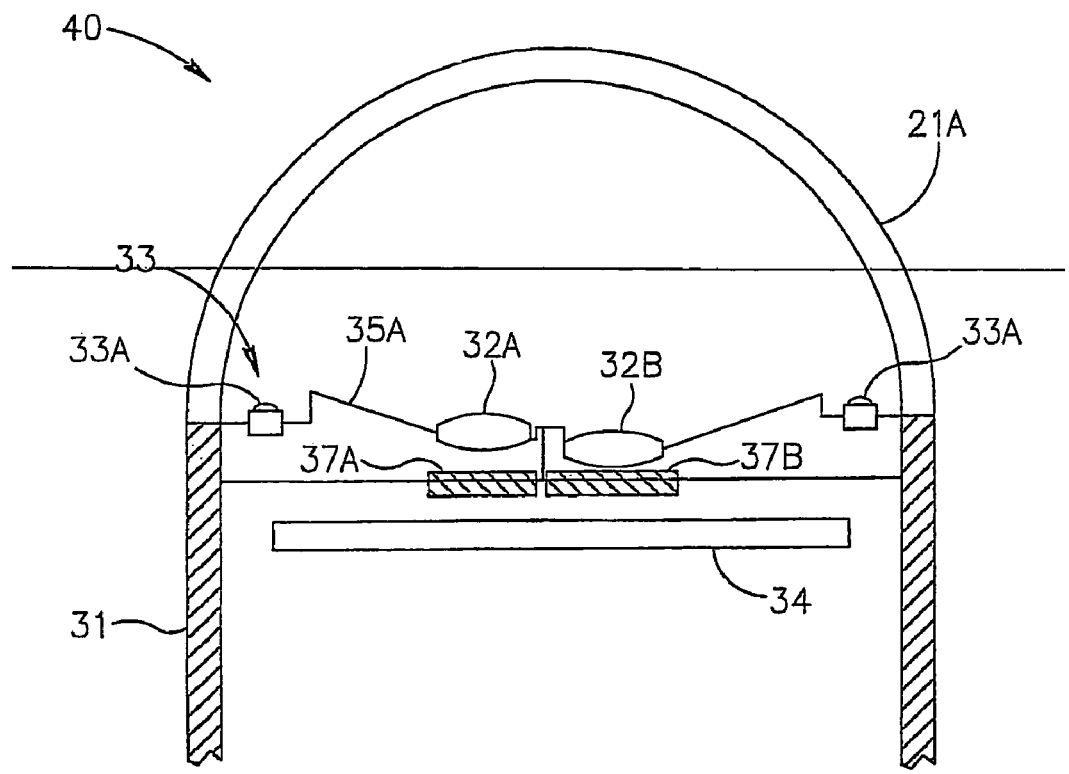
FIG. 3 is a schematic cross-sectional view of part of an in-vivo imaging device having two shuttered optical systems and a single imager, in accordance with another preferred embodiment of the present invention.

Reference is now made to FIG. 3, which is a schematic cross-sectional view of part of an in-vivo imaging device having two optical systems and a single imager, in accordance with another preferred embodiment of the present invention.

The in vivo imaging device 40 includes an imaging sensor 34. The imaging sensor 34 may be a CMOS pixel array sensor similar to the CMOS imaging sensor 24 of FIG. 1, or may be any other type of suitable imaging sensor known in the art.

The device 40 includes a housing 31 and an optical window 21A attached to the housing 31, as disclosed hereinabove and illustrated in FIG. 2. If the device 40 is implemented as a swallowable capsule, the housing 31 may be a capsule-like housing, as disclosed in detail in U.S. Pat. No. 5,604,531 to Iddan et al., and/or in WO 01/65995 to Glukhovsky et al. If the device 40 is implemented as an endoscope-like device or a catheter-like device, the housing 31 may be an extended elongated flexible device (the extended device is not shown in its entirety for the sake of clarity of illustration). Such devices may be shaped as elongated flexible devices for insertion into a body cavity or body lumen of a human patient or an animal.

The optical window 21A may be a transparent optical dome as disclosed in WO 00/76391 to Glukhovsky et al. but may be any type of suitable optical window.

The device 40 may include an illumination unit 33, which may include one or more light sources 33A, as disclosed hereinabove. The light sources 33A may be "white" LED sources but may also be any other light sources suitable for providing illumination for in vivo imaging, such as but not limited to the light sources disclosed in U.S. Pat. No. 5,604,531 to Iddan et al. The device 40 may include two optical systems 32A and 32B. The optical systems 32A and 32B may be attached to or mounted in a baffle 35A, or otherwise suitably attached to the housing 31 of the device 40 or to any other suitable structure included in the device 40 (such as, for example, to the imaging sensor 34). The baffle 35A may be shaped to prevent light emitted from the light sources 33A from directly reaching the optical systems 32A and 32B, while allowing light reflected from the imaged object, such as but not limited to, the intestinal wall (not shown) to reach the optical systems 32A and 32B.

The imaging sensor 34 may be disposed adjacent to the optical systems 32A and 32B, or may be also attached thereto.

The optical systems 32A and 32B may be single lenses, composite (multi-element) lenses, or any suitable combination of optical elements which are suitable for forming images of the imaged object, (such as but not limited to, the intestinal wall) and projecting the images onto the surface of the imaging sensor 34.

The depth of field range of the optical system 32A is different than the depth of field range of the optical system 32B. For example, the focal length of the optical system 32A may be longer than the focal length of the optical system 32B. Each of the optical systems 32A and 32B projects an image on the surface of the imaging sensor 34. In contrast to the arrangement of the optical components illustrated in FIG. 2, the images projected by the optical system 32A and 32B on the imaging sensor 34 of the device 40 may overlap.

The device 40 further includes two controllable light switching units 37A and 37B. According to an embodiment of the invention the controllable light switching unit 37A is interposed between the optical system 32A and the imaging sensor 34. The controllable light switching unit 37B is interposed between the optical system 32B and the imaging sensor 34. Preferably, but not necessarily, the controllable light switching units 37A and 37B may be electro-optical devices which may be electrically (or magnetically) controlled to block or enable the passage of light therethrough. For example, the controllable light switching units 37A and 37B may be electrically controllable liquid crystal shutters (LCS), electrically controllable ferroelectric optical shutters, high-speed electrolytic optical shutters, electro-optical shutters based on the Kerr and Pockels effects, or optical shutter devices based on ferroelectric films or ferroelectric liquids or on ferroelectric crystals or any other suitable electro-optical or magneto-optical shutter known in the art. The controllable light switching units 37A and 37B may also be any suitable controllable electro-mechanical shutter devices known in the art.

In operation, the controllable light switching units 37A and 37B may be used to provide exposure of the imaging sensor 34 to light projected by a selected one of the optical systems 32A and 32B. This selection is typically needed due to the at least partial overlap of the images projected on the surface of the imaging sensor 34 as shown hereinafter.

Figure 3A:
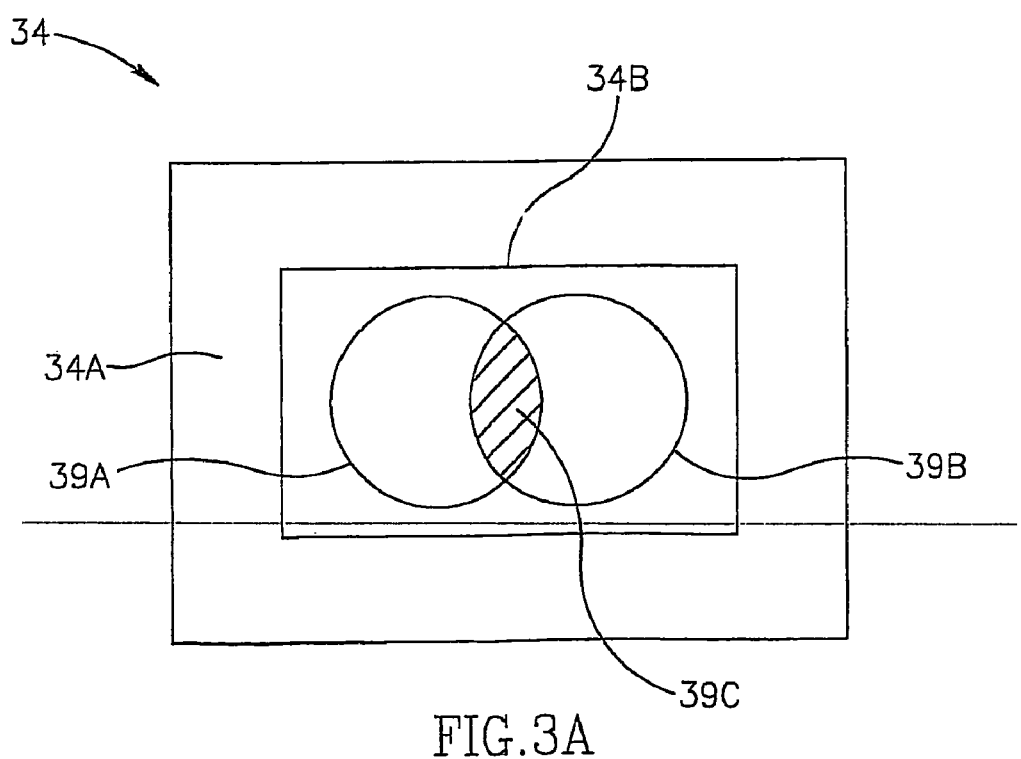
FIG. 3A is a schematic front view of the surface of the imaging sensor of the device illustrated in FIG. 3, schematically illustrating the degree of overlap of images which may be projected on the surface of the imaging sensor if both shutters are opened.

Reference is now briefly made to FIG. 3A which is a schematic front view of the surface of the imaging sensor of the device illustrated in FIG. 3, schematically illustrating the degree of overlap of images which may be projected on the surface of the imaging sensor if both light switching units (shutters) are opened, according to an embodiment of the invention.

In FIG. 3A, the surface 34A represents a top view of the surface of the entire imaging sensor 34. The surface 34B schematically represents the imager area part comprising the light sensitive pixels (the pixels are not shown in detail). The part of the imager surface surrounding the area 34B may include the support circuitry for performing readout of the pixels and other electronic support circuitry such as clocking circuitry and the like, as is known in the art. The partially overlapping circular areas 39A and 39B schematically represent the area of the images projected on the surface 34B by the optical systems 32A and 32B, respectively. The areas 39A and 39B overlap. The hatched area 39C represents the area of overlap between the image projected on the surface 34B by the optical system 32A and the image projected by the optical system 32B on the surface 34B.

It is noted that the image overlap shown may occur only in a situation in which both of the light switching units 37A and 37B are switched to allow passage of the light coming from the corresponding optical systems 32A and 32B to reach the surface 34B of the imaging sensor 34. This typically does not normally occur during operation of the device 40, since the purpose of the light switching units 37A and 37B is typically to prevent the simultaneous exposure of the surface 34B to light projected from both optical systems 32A and 32B.

Thus, in operation, during active imaging, the illuminating unit 23 may be switched on to provide illumination for an imaging cycle. An imaging cycle may comprise a first imaging time period in which the light switching unit 37A may be controllably switched on to allow the light collected by the optical system 32A to be projected on the surface 34B of the imaging sensor 34 while during the same first imaging time period the light switching unit 37B is switched off such that light projected from the optical system 32B is blocked by the light switching unit 37B and does not reach the surface 34B of the imaging sensor 34. In the first time period a first image projected by the optical system 8 is acquired.

After the first image projected by the optical system 32A is acquired by scanning (readout) of the pixels of the imager 34, the image data may be stored in a memory device (not shown) included in the device 40 for later transmission, or may be directly transmitted to an external receiver/recorder as disclosed hereinabove. After the acquired image data is stored in a memory device or is transmitted to an external receiver/recorder, a second imaging time period may be started. During the second imaging time period, the light switching unit 37B may be controllably switched on to allow the light collected by the optical system 32B to be projected on the surface 34B of the imaging sensor 34 while during the same second time period the light switching unit 37A is switched off such that light projected from the optical system 32A is blocked by the light switching unit 37B and does not reach the surface 34B of the imaging sensor 34. In the second imaging time period a second image projected by the optical system 32B is acquired. After the end of the imaging cycle, which may be the time of termination of the second imaging time period, the illumination unit 23 may be turned off.

After the second image projected by the optical system 32B is acquired by scanning (readout) of the pixels of the imager 34, the image data may be stored in a memory device (not shown) included in the device 40 for later transmission, or may be directly transmitted to an external receiver/recorder as disclosed hereinabove.

If the first image data and the second image data have been stored in a memory device (not shown) the data of the first and the second acquired images may be transmitted to the receiver/recorder. Alternatively, the first and the second acquired images may be transmitted after the second imaging time period is terminated.

The data transmitted may be stored in the receiver/recorder device (not shown) for later processing and display. Thus, each imaging cycle of the device 40 may yield two different images of approximately (but not necessarily exactly) the same imaged object.

It will be appreciated that while the imaging method used in the device 30 (FIG. 2) may yield two images acquired simultaneously within a single imaging cycle through two different optical systems having a different depth of focus range, the imaging method used in the device 40 (FIG. 3) may yield two images sequentially acquired through two different optical systems having a different depth of focus range. If the device 40 does not move (remains stationary) within the duration of the imaging cycle, the images may represent approximately the same object or imaged area (which may however be imaged with different field of view due to the different field of view of the optical systems 32A and 32B). If the imaging device 40 moves during the imaging cycle, the first and second images acquired may not show the same object or the object may be shifted in the second image relative to the first image. The degree of the shift may depend, inter alia, on the duration of the imaging cycle, the velocity of the imaging device 40 relative to the imaged object (such as, for example, the intestinal wall), the distance to the imaged object, and the focal length of the optical systems 32A and 32B.

Preferably, the duration of the imaging cycle should be short to prevent or reduce image blurring or smearing (which may occur due to device movement in both of the devices 30 and 40), and to reduce or prevent shift of the imaged objects which may occur in the device 40 due to the sequential acquisition of the first image and the second image in an imaging cycle.

Thus, while the device 30 has the advantage of not being subject to the image shift as disclosed hereinabove, it may have lower image resolution since two images are simultaneously acquired on the surface 34B of the imaging sensor 34 with no image overlap which reduces the number of pixels within each of the two images. The device 40 may have the advantage of higher resolution for each image because only one image may be acquired at the same time, allowing better use of the available surface 34B of the imaging sensor 34 in that each of the two images which are acquired sequentially may have a higher pixel number than the images acquired simultaneously in the device 30. The device 40 may however be more susceptible to image shifting caused by movement of the device 40 within the duration of a single imaging cycle. This image shift may be reduced by reducing the duration of the imaging cycle or by reducing the time of acquisition of each of the two images within the imaging which may be achieved, inter alia, by using an imaging sensor having a high sensitivity.

Because of the different focal length of the two different optical systems 32A and 32B, even if one image part is not properly focused the other image part may be in better focus due to the larger depth of field range of the optical system having the shorter focal length. Thus, the chance of obtaining at least one acceptably focused image within a single imaging cycle of in-vivo imaging devices 30 and 40 is increased relative to the chance in a similar in vivo imaging device which includes only a single optical system.

It is noted that while the overlap (illustrated in FIG. 3A) between the areas 39A and 39B of FIG. 3A is partial, the optical systems 32A and 32B of the device 40 may be configured such that the areas 32A and 39B may fully overlap. This may be achieved if desired by suitable configuring of the optical systems 32A and 32B of the device 40 as is known in the art or by introducing additional optical elements (not shown) to ensure overlap of the two areas 39A and 39B. The advantage of full overlap is that such a design enables a better utilization of the surface 34B which includes the light sensitive pixel elements, and may achieve a higher resolution for both images without reducing the image size.

Figure 4:
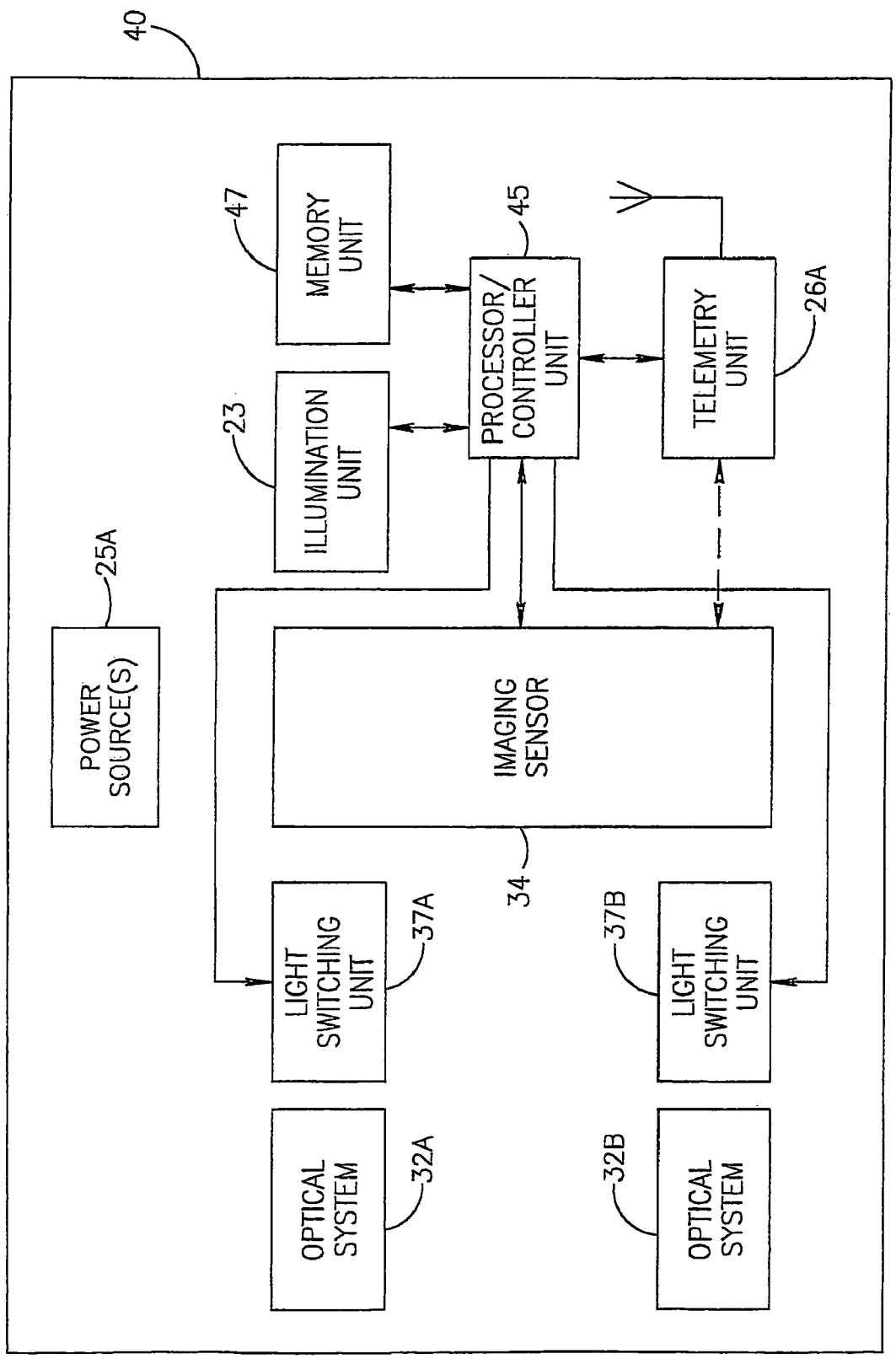
FIG. 4 is a schematic functional block diagram useful in understanding the components of the device partially illustrated in FIG. 3, according to an embodiment of the invention.

Reference is now made to FIG. 4, which is a schematic functional block diagram useful in understanding the operation of the device illustrated in FIG. 3 and, possibly with some modifications (e.g., possibly removal of units 37A and 37B) FIG. 2.

The device 40 may include one or more power sources 25A for supplying power to the components included in the device 40. The device 40 may include a processor/controller unit 45. The processor/controller unit 45 may be suitably connected to an imaging sensor 34 for controlling the operation of the imaging sensor 34 and for (optionally) receiving the image data from the imaging sensor 34. The imaging sensor 34 may be (optionally) suitably connected to a telemetry unit 26A. The telemetry unit 26A may receive the data or signals read out from the imaging sensor 34 and transmit the signals or data (with or without further processing) to a receiver/recorder (not shown in FIG. 4) as is disclosed in detail hereinabove. The telemetry unit 26A may operate similar to the transmitter 26 coupled to the antenna 27 of FIG. 1. The device 40 may further include two different optical systems 32A and 32B having different depth of focus range as disclosed hereinabove and illustrated in FIG. 3.

A light switching unit 37A may be interposed between the optical system 32A and the light sensitive surface of the imaging sensor 34. Another light switching unit 37B may be interposed between the optical system 32B and the light sensitive surface of the imaging sensor 34. The light switching units 37A and 37B are suitably connected to the controller/processor unit 45 and may receive control signals therefrom for switching the light switching units 37A and/or 37B on and off. The switching signals may be digital signals, or may be analog voltage signals produced by a suitable interface unit (not shown), but may however be any other suitable control signals known in the art for switching the switching units on or off. In alternate embodiments, control may be provided in other manners, using other components or combinations of components. For example, the telemetry unit 26A may provide control.

Figure 1:
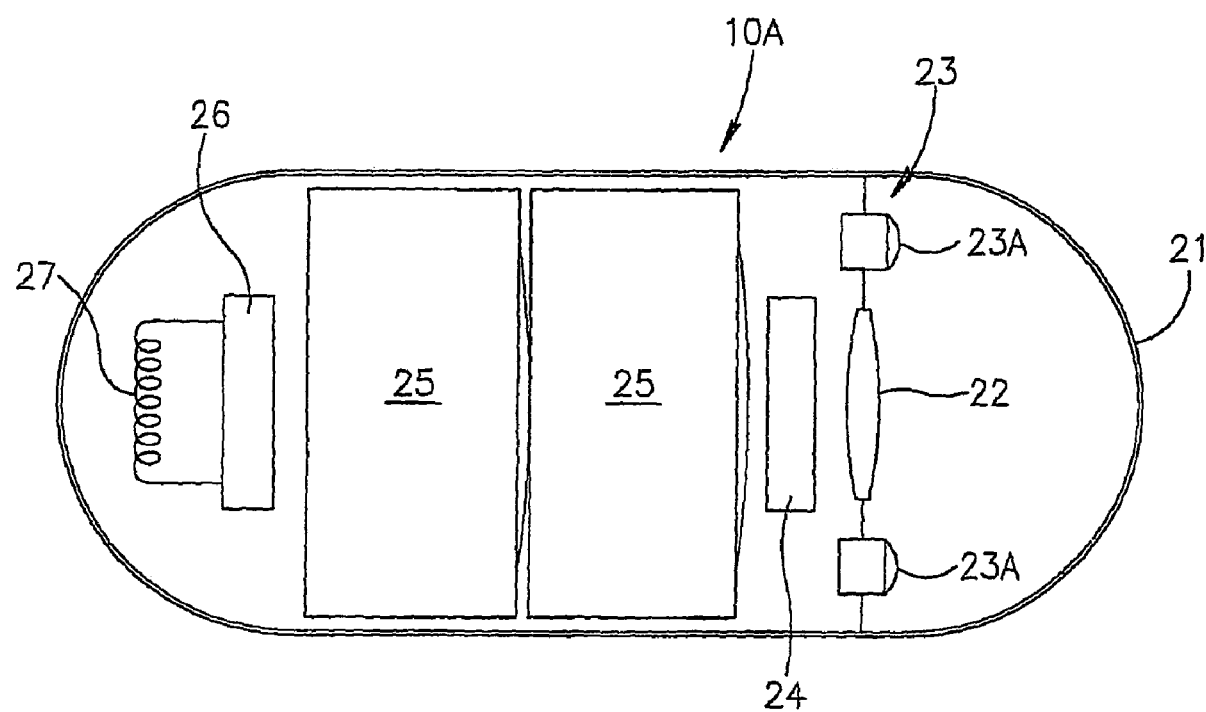
FIG. 1 is a schematic diagram illustrating an embodiment of an autonomous in-vivo imaging device.

The device 40 includes an illuminating unit 23 as disclosed in detail hereinabove and illustrated in FIGS. 1, 2, and 3. The illumination unit may be suitably connected to the processor controller unit 45 for receiving control signals therefrom. The processor controller unit 45 may control the operation of the illumination unit 23 by switching it on or off as necessary.

The device 40 may (optionally) include a memory unit 47 suitably connected to the processor/controller unit. The memory unit 47 may be (optionally) used to store acquired image data which is read out from the imaging sensor 34.

It is noted that the imaging sensor 34 may or may not include further processing circuitry (not shown) which may be used for performing imaging various support functions such as synchronization and clocking functions, pixel scanning functions and other functions associated with imaging sensor which are known in the art of imaging sensors. Additionally, the imaging sensor 34 may also include analog to digital converting circuitry (not shown in detail) for providing digital signals to the processor/controller unit 45. Alternatively, a separate analog to digital converter (not shown) may (optionally) couple the imaging sensor 34 to the processor/controller unit 45.

For performing an imaging cycle, the device 40 may be operated as follows. At the beginning of each imaging cycle, the processor/controller unit 45 may switch on the light switching unit 37A and may simultaneously switch off the light switching unit 37B to allow light focused by the optical system 32A to be projected onto the surface of the imaging unit 34 while blocking the light focused by the optical system 32B from reaching the surface of the imaging unit 34. Simultaneously with the switching of the light switching unit 37A on, the processor/controller unit 45 may switch on the illumination unit 23 to illuminate the imaged object (not shown). After the end of the first imaging period, the processor/controller unit 45 may store the acquired first image in the memory unit 47 or may alternatively control the transmission of the acquired image to a receiver/recorder (not shown).

If the first image data is transmitted by the telemetry unit 26A after image acquisition, the illumination unit 23 may be turned off for the duration of the transmission time period to conserve power and to reduce the current drain from the power source(s) 25A. In such a case, the processor/controller unit 45 may switch the illumination unit on again after the data has been transmitted. Simultaneous with switching the illumination unit on the processor/controller unit 45 may also switch on the light switching unit 37B and may switch off the light switching unit 37A. In this way the light focused by the optical system 32B is now allowed to reach the surface of the imaging sensor 34 for the duration of a second imaging time period and a second image is acquired. After the termination of the second imaging period, the illumination unit 23 may be turned off by the processor/controller unit 45. The second acquired image may then be transmitted by the telemetry unit 26A as disclosed hereinabove. The device 40 may then be ready for another imaging cycle.

If the device 40 has image storage capacity (such as by including the memory unit 47 of FIG. 40), the first acquired image may be stored in the memory unit 47 while the pixels readout of the imaging sensor 34 is performed. In such a case, the processor/controller unit 45 may turn off the illuminating unit 23 at the end of the first imaging period and may turn the illuminating unit 23 on again after the image data readout has been completed and the imaging sensor has been reset for enabling the acquiring of a second image. In such a case, the data of the second image acquired within the imaging cycle may be also stored in the memory unit 47 and the data of the first acquired image and the second acquired image may be transmitted by the telemetry unit 26A. The stored data of the first and second acquired images may be transmitted sequentially. Other forms of transmission may however also be possible. For example, it may be possible to transmit data from the first and second images in an interleaved manner.

It is noted, however, that if the device 40 includes a memory device such as the memory unit 47, it may also be possible to start transmitting the stored data of the first acquired image before the acquisition of the second image has been completed. For example, the telemetry unit 26A may be controlled to start the transmission of the first image data as soon as some data for the first image is stored in the memory device 47. Such transmission may be controlled and timed by the processor/controller 45. The advantage of this transmission method is that it may enable transmission of the first image data while acquisition of the second image data is being performed, which may enable the repeating of the imaging cycles at a higher frequency than the frequency possible in the method in which both the first and the second image data are transmitted sequentially only after the acquisition of both the first and the second images has been completed.

It is noted that the memory unit 47 may be, a random access memory unit (RAM) but any other suitable type of memory device or unit known in the art may be used. The memory unit 47 may be a separate memory unit suitably coupled or connected to the processor/controller unit 45 or may be a memory unit included in the same integrated circuit (IC) on which the processor/controller unit 45 is made, which may obviate the need for connecting a separate memory unit to the processor/controller unit 45.

It is further noted that it may be possible to fabricate some or all of the electronic circuitry or electronic components illustrated in FIG. 4 on the same Integrated circuit. Thus, for example, it may be possible to fabricate two or more of the processor/controller 45, the memory unit 47, and the telemetry unit 26A oh the same IC to save space and to simplify assembly of the device 40. It may also be possible to fabricate one or more of the processor/controller 45, the memory unit 47, and the telemetry unit 26A on the same IC on which the imaging sensor 34 is fabricated.

It will be appreciated by those skilled in the art, that while the devices 30 and 40 are devices that include two optical systems 32A and 32B, other embodiments of the invention may be constructed, which include more than two optical systems (not shown). In accordance with one embodiment of the invention, such devices may have no light switching units and may operate by simultaneous acquisition of more than two non-overlapping images. In accordance with another embodiment of the invention, such devices may have light switching units and may operate by sequential imaging of potentially overlapping images.

It may also be possible to use a combination of the operating methods disclosed hereinabove in an imaging device having a plurality of optical systems. For example, in accordance with an embodiment of the present invention the in vivo imaging device may include three optical systems (not shown). A first optical system and a second optical system of the three optical systems may project potentially overlapping or partially overlapping images on the surface of the imaging sensor (not shown). These first and second optical systems may be associated with two light switching elements (not shown) which may be used as disclosed hereinabove to sequentially acquire the two images sequentially projected on the imaging sensor. The third optical system (not shown) may project a third image on the surface of the imaging unit. This third image may be non-overlapping with the first and the second images. The third image may thus be acquired simultaneously with the first image projected by the first optical system, or (alternatively) simultaneously with the second image projected by the second optical system.

While the invention has been described with respect to a limited number of embodiments, it will be appreciated that many variations, modifications and other applications of the invention may be made which are within the scope and spirit of the invention.

The invention claimed is:

1. An in vivo imaging device comprising:
   an illumination source;
   an image sensor;
   at least two optical systems oriented in substantially the same direction, a first of said optical systems having a first depth of focus and configured to focus at least a first image onto said image sensor, a second of said optical systems having a second depth of focus and configured to focus a second image onto said image sensor; and
   a first light switching unit interposed between the first of the at least two optical systems and the image sensor, and a second light switching unit interposed between the second of the at least two optical systems and the image sensor, wherein the first and second light switching units are operable to block or enable the passage of light therethrough; and
   wherein said in vivo imaging device is a swallowable capsule.

2. The device according to claim 1 wherein the at least first and at least second image do not overlap.

3. The device according to claim 1 wherein the at least first and at least second image at least partially overlap.

4. The device according to claim 1 wherein at least a first light switching unit is switched on during a first imaging time period and wherein a second light switching unit is switched on during a second imaging time period.

5. A device according to claim 4 wherein the first light switching unit is switched off after the first imaging time period and wherein the second light switching unit is switched off after the second imaging time period.

6. The device according to claim 1 comprising a controller to control the switching of at least one light switching unit.

7. The device according to claim 1 comprising a memory device.

8. The device according to claim 1 comprising a transmitter.

9. A method for obtaining in vivo images, the method comprising the steps of:
   focusing light remitted from an in vivo site onto an image sensor through at least a first optical system having a first depth of focus;
   focusing light remitted from the in vivo site onto said image sensor through at least a second optical system having a second depth of focus oriented in substantially the same direction as said first optical system;
   wherein a first light switching unit is interposed between the first optical system and the image sensor, and a second light switching unit is interposed between the second optical system and the image sensor; and
   controlling the first and second light switching units to block or enable the passage of light therethrough.

10. The method according to claim 9 comprising reading out image data into a memory device.

11. The method according to claim 9 further comprising transmitting image data from the memory device to an external receiving unit.

12. The method according to claim 9 further comprising a step of transmitting image data to an external receiving unit.

13. The method according to claim 9
   wherein said step of focusing light remitted from an in vivo site by an image sensor through at least a first optical system having a first depth of focus is preformed during a first imaging time period; and
   wherein said step of focusing light remitted from the in vivo site by the image sensor through at least a second optical system having a second depth of focus oriented in substantially the same direction as said first optical system is preformed during a second imaging time period.

14. The method according to claim 13 further comprising reading image data into a memory device.

15. The method according to claim 13 comprising transmitting image data.

* * * * *